(12) United States Patent
Lee et al.

(10) Patent No.: US 10,492,727 B2
(45) Date of Patent: Dec. 3, 2019

(54) BIOMEDICAL DEVICE, SYSTEMS AND METHODS HAVING CONDUCTIVE ELEMENTS

(71) Applicant: Johnson & Johnson Consumer Inc., Skillman, NJ (US)

(72) Inventors: Curtis Lee, Philadelphia, PA (US); Ryan Walsh, Douglassville, PA (US); Alan Trojanowski, Monmouth Junction, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/711,123

(22) Filed: Sep. 21, 2017

(65) Prior Publication Data

US 2018/0008199 A1 Jan. 11, 2018

Related U.S. Application Data

(62) Division of application No. 14/108,012, filed on Dec. 16, 2013, now Pat. No. 10,292,654.

(51) Int. Cl.
*A61B 5/1455* (2006.01)
*A61B 5/00* (2006.01)
*A61B 5/0205* (2006.01)

(52) U.S. Cl.
CPC ........ *A61B 5/6831* (2013.01); *A61B 5/02055* (2013.01); *A61B 5/14552* (2013.01)

(58) Field of Classification Search
None
See application file for complete search history.

(56) References Cited

U.S. PATENT DOCUMENTS 5,517,987 A 5/1996 Tsuchiya
6,519,487 B1 2/2003 Parker
(Continued)

FOREIGN PATENT DOCUMENTS

JP 2002224088 A 8/2002

OTHER PUBLICATIONS

International search report and written opinion dated Mar. 4, 2015, for international patent application No. PCT/US2014/066106.

*Primary Examiner* — Eric F Winakur
*Assistant Examiner* — Marjan Fardanesh

(57) ABSTRACT

A device for determining a physiological property of a body includes an insulating support having a compliant contact surface with a conductive element to contact the body. A mounting fixture disposed over a mounting surface of the support removably holds a rigid sensor spaced apart from the body and coupled to the conductive element to determine the physiological property via that element. A method for enabling a physiological parameter to be measured without direct contact between an active device and the body includes arranging a conductive element over an inner surface of an insulating circumferential band. A sensor with the active device is attached to the exterior of the band and thus coupled to the element. A system includes the sensor having a mounting connector, and sensor carriers with respective supports, mounting fixtures, and conductive elements. The sensor mounted on a carrier determines the property via the respective conductive element.

5 Claims, 11 Drawing Sheets

(56) References Cited

U.S. PATENT DOCUMENTS

| | | |
|---|---|---|
| 6,699,199 B2 | 3/2004 | Asada et al. |
| 7,324,841 B2 | 1/2008 | Reho et al. |
| 8,250,796 B2 | 8/2012 | Padgett et al. |
| 8,263,986 B2 | 9/2012 | Hajj-Hassan et al. |
| 2004/0220485 A1 | 4/2004 | Rytky |
| 2005/0049474 A1 | 3/2005 | Kellogg et al. |
| 2008/0004510 A1* | 1/2008 | Tanzawa ............... A44C 5/0015 600/301 |
| 2010/0033303 A1 | 2/2010 | Dugan et al. |
| 2011/0112793 A1 | 5/2011 | Biebold et al. |
| 2012/0179067 A1 | 7/2012 | Wekell |
| 2012/0247179 A1 | 10/2012 | Kerin et al. |
| 2013/0324860 A1 | 5/2013 | Borgos et al. |
| 2015/0164422 A1 | 6/2015 | Lee et al. |

* cited by examiner

BIOMEDICAL DEVICE, SYSTEMS AND METHODS HAVING CONDUCTIVE ELEMENTS

CROSS-REFERENCE TO RELATED APPLICATIONS

This application is a divisional of U.S. application Ser. No. 14/108,012 filed on Dec. 16, 2013, the complete disclosure of which is hereby incorporated herein by reference for all purposes.

TECHNICAL FIELD

This application relates generally to the field of electronic systems for monitoring biological properties of a user's body, and more specifically to sensors used in such systems.

BACKGROUND

The use of various types of sensors to evaluate one or more physiological parameters of a patient is well known. For example, optical pulse oximetry sensors measure the level of oxygen saturation ($SpO_2$) in a patient's blood. In one such sensor, a light-emitting diode (LED) transmits optical radiation of several different wavelengths, e.g., visible and infrared, through blood and tissue of a predetermined portion of a patient's body; typically, the wrist or finger. A photodetector detects the light (human-visible or other wavelengths) after it passes through the body. Different wavelengths of light are absorbed differently based on blood oxygen content, so detecting the optical attenuation at each wavelength permits determining oxygen saturation. In another example, electrocardiogram (ECG or EKG) electrodes are generally planar electrodes connected via wires to an ECG unit that measures the voltage across different pairs of the electrodes to monitor the patient's heart. It is generally required that physiologic sensors be correctly placed with respect to a specific body part to be measured. For example, a pulse oximetry sensor should be placed so that the optical path from the transmitter to the detector intersects a blood vessel. Likewise, an ECG sensor should be placed on a part of the body that provides effective electrical contact across the skin (e.g., not on top of significant amounts of hair). It is also generally required that the sensor effectively contact the patient's body to make accurate measurements.

Many types of sensors are rigid or are fabricated at least in part using rigid substrates. However, specific areas of the human body change shape while moving, e.g., as muscles alternately contract and relax. In order to maintain contact of a rigid sensor to a flexible body, some prior schemes describe bands carrying the sensors, or sensors embedded in clothing. However, these schemes are limited in the accuracy with which they can maintain position. Other schemes apply pressure to a body part, e.g., by pressurizing the inside of a ring on a patient's finger, to retain the sensor in position with respect to that body part. However, these schemes can require expensive supports for the sensors and can cause increased patient discomfort. Alternative schemes permit the sensor to move with respect to the body part, then compensate for that motion.

Even if the sensor is retained in place with respect to the body, or motions are compensated for, it is still desirable for the sensor to effectively contact the body. For example, a skin conductance sensor has two electrodes that contact the skin to measure the resistance or voltage between the two electrodes. Since these electrodes are directly in contact with the skin in conventional systems, the electrodes can become contaminated with, e.g., oil, water, or salt over time. This contamination can reduce the accuracy of the sensor. It is known to clean sensors periodically. However, every cleaning cycle can cause water damage or other types of wear to the sensor or its electrodes. Moreover, recalibration of the sensor may be required after cleaning to correct for this wear.

SUMMARY OF THE DISCLOSURE

In one embodiment, therefore, we have devised a device for determining a physiological property of a body. The device may include the following components:
  a) an insulating support having a compliant contact surface and an opposed mounting surface, so that the contact surface is configured to contact the body;
  b) at least one conductive element arranged at least partly on or over the contact surface;
  c) a mounting fixture disposed over the mounting surface; and
  d) a rigid sensor removably mounted in the mounting fixture, so that the rigid sensor is spaced apart from the body and is coupled to the at least one conductive element to determine the physiological property of the body via the at least one conductive element.

In another embodiment, we have devised a method for enabling a physiological parameter to be measured or monitored without direct contact between an active device and a body. The method can be achieved by:
  receiving a substantially-insulating circumferential band having a skin-contacting inner surface and an exterior surface;
  disposing at least one conductive element within the circumferential band, the at least one conductive element at least partly arranged on or over the inner surface of the band; and
  attaching a sensor retaining the active device to the exterior surface of the band so that the active device is coupled to the at least one conductive element.

In another embodiment, we have devised a physiological monitoring system. The system may include the following components:
  a) a rigid sensor having a mounting connector;
  b) a plurality of sensor carriers, each having:
    i) an insulating support adapted to retain the sensor carrier in position with respect to a respective part of a body, the support having a compliant contact surface to contact the respective part of the body;
    ii) a mounting fixture to releasably retain the mounting connector; and
    iii) a conductive element arranged at least partly on or over the contact surface, so that the rigid sensor mounts in the mounting fixture of one of the sensor carriers to determine a physiological property of the body via the corresponding conductive element.

These embodiments exemplary of the present invention provide improved feedback regarding sensor positioning. Various embodiments advantageously provide users and home-care providers ways of positioning sensors accurately. Various embodiments provide detection of conditions that may interfere with sensor readings.

Accordingly, in any of the embodiments described earlier, the following features may also be utilized in various combinations with the previously disclosed embodiments. For example, the devised a device for determining a physiological property of a body can include the at least one conductive element having at least two conductive elements coupled to respective interfaces of the rigid sensor so that the rigid sensor determines the physiological property of the body by providing an excitation to the body via a first selected one of the at least two conductive elements and receiving a response of the body to the provided excitation via a second selected one of the at least two conductive elements. The at least one conductive element can extend at least in part radially through the support. The rigid sensor can be coupled to a first end of the at least one conductive element, the at least one conductive element extending along the contact surface so that the rigid sensor determines the physiological property of the body at an opposite second end of the conductive element. The at least one conductive element can include a plurality of conductive elements extending along the contact surface and having respective first ends coupled to respective interfaces of the rigid sensor, the second ends of at least two of the plurality of conductive elements being spaced apart from each other. The at least one conductive element may include a light pipe extending along the contact surface. The mounting fixture can include a slot adapted to receive a mounting tab protruding from the rigid sensor. The at least one conductive element can be electrically conductive, the insulating support can be electrically insulating, and the rigid sensor can include an electrical contact interface coupled to the at least one conductive element. The at least one conductive element can be optically conductive at a selected wavelength, and the rigid sensor can include an electro-optical interface coupled to the at least one conductive element. The rigid sensor can include an optical filter disposed between the conductive element and the electro-optical interface. The device can include at least one aperture extending through the support, the rigid sensor including a second conductive element extending through the aperture to determine the physiological property of the body. The rigid sensor can include a transceiver configured to communicate determined physiological data to a host processor. The support can be defined by a circumferential band configured to be wrapped about a portion of the body, the contact surface being configured to contact the skin of the body. The support may include a plurality of substantially-insulating, interlocking modules, and at least one of the plurality of modules can include a mounting surface having a mounting fixture. At least one of the plurality of modules being different from at least one other interconnecting module wherein a contact surface of at least one module consists of insulating material. A first of said modules can include the mounting fixture having a first rigid sensor and a second of the modules can include a second rigid sensor configured to cooperate with the first rigid sensor to determine the physiological property of the body via the at least one conductive element. The physiological property can be a blood oxygen content, the rigid sensor can include one of a light emitter or a photodetector, the second rigid sensor can include the other of the light emitter or the photodetector, and the selected one of the modules and the second selected one of the modules can be arranged so that at least some light emitted by the light emitter passes through a part of the body and reaches the photodetector. A second selected one of the modules can include a second rigid sensor configured to determine a second physiological property of the body different from the physiological property. The interlocking modules can be arranged to form a circumferential band wherein the second module is diametrically opposite to the first module. Two interlocked modules of the support can include respective conductors configured to convey signals between each other. The conductive element can include one or more conductive segments arranged in various connected modules.

In various examples, the method can include activating the sensor to provide a signal to the body and receive a response of the body to the provided signal. The at least one conductive element can include a plurality of conductive elements and the method can further include attaching a second sensor retaining a second active device to the exterior surface of the band, so that the second sensor is coupled to one of the plurality of conductive elements. The method can include activating the sensor to provide a signal to the body and activating the second sensor to receive a response of the body to the provided signal. The method can include detaching the sensor from the exterior surface of the band and attaching a second, different sensor in place of the detached sensor.

In various examples, the physiological monitoring system can include each mounting fixture having a quick-disconnect receptacle and the mounting connector of a sensor having a mating quick-disconnect plug. Each sensor carrier can be defined by a circumferential band configured to wrap around a part of the body. Each sensor carrier can be made from disposable materials.

In the aforementioned aspects of the disclosure, the steps of receiving disposing, attaching, activating, or detaching (possibly in conjunction with an equation or an industrial robot) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, direct a robot to perform the steps of any one of the aforementioned methods, e.g., the attaching or detaching steps; or perform steps such as the activating steps.

In additional aspects of the disclosure, there are devices, such as sensors, or smartphones or other user-interface devices, each comprising an electronic circuit or processor configured to perform steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention. For the sake of clarity, like reference numerals herein represent like elements.

FIGS. 3A and 3B are perspective views of an exemplary sensor and insulating support in which FIG. 3A shows the components individually and FIG. 3B shows the components in a coupled configuration;

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the term "body" is intended to be used in the context of any part of a person; the terms "about" or "approximately" for any numerical values or ranges indicate a suitable dimensional tolerance that allows the part or collection of components to function for its intended purpose as described herein. More specifically, "about" or "approximately" may refer to the range of values not at least ±10% of the recited value, e.g. "about 90%" may refer to the range of values from 81% to 99%. As used herein, the phrase "electrical signal" or "signal" is intended to include direct current signals, alternating signals or any signal within the electromagnetic spectrum. The terms "processor," "microprocessor," and "microcontroller" are intended to have the same meaning and are intended to be used interchangeably. Throughout this disclosure, the terms "patient" and "subject" are used interchangeably. These terms can refer to any human or animal subject and are not intended to limit the systems or methods to human use, although use of aspects described herein with a human patient represents a preferred embodiment. Furthermore, in this disclosure, the term "user" can refer to a patient using a biosensor or another person (e.g., a parent or guardian, nursing staff member, home care employee, or other caretaker) using such a device. The term "healthcare provider" or "HCP" refers generally to doctors, nurses, and individuals other than the patient that provide health care services to the patient.

Various embodiments described herein advantageously permit collecting accurate sensor data of the body without fouling or prematurely aging the biosensors. Various embodiments retain the sensor in position in a way that is comfortable to the user. These permit measuring more-consistent, more-reliable sensor data, which in turn can improve user perceptions of the trust that can be placed in the system.

Figure 1A:
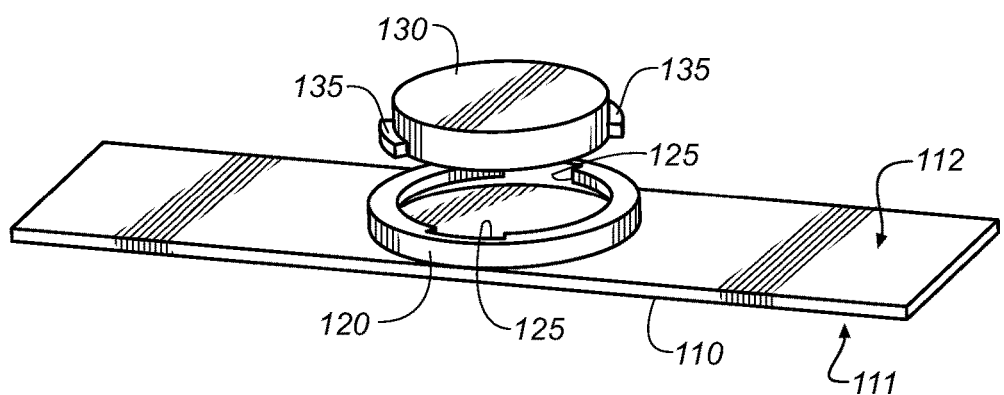
FIG. 1A is a perspective view of an exemplary device for determining a physiological property of a body, including a sensor and an insulating support.

FIG. 1A is a perspective of an exemplary device for determining a physiological property of a body. The device includes an insulating support 110 having a compliant contact surface 111 and an opposed mounting surface 112. The contact surface 111 is configured to contact a body 1138, FIG. 11, e.g., the body of a patient. According to at least one version, the mounting surface 112 can also be compliant, though this is not required. The insulating support 110 can be shaped in the form of a circumferential member such as a ring, bracelet, band (e.g., headband, armband, leg band, or waistband), or slap bracelet that can be disposed onto a body of a patient. For purposes of compliancy, the insulating support 110 or the contact surface 111 thereof can be manufactured or formed from elastomeric materials such as silicones, thermoplastic elastomers (TPE), thermoplastic vulcanates (TPV), polyurethanes, or like materials that provide similar compliant characteristics. Such materials can have Shore A hardness from about 10 to about 40. The insulating support 110 can have a thickness between the contact surface 111 and the mounting surface 112 of between about 2 mm and about 5 mm. Using elastomeric or other compliant materials can provide improved conformability of the support 110 to the body 1138 as the body 1138 changes shape, and can provide improved comfort and washability compared to more rigid materials.

A mounting fixture 120 is disposed over the mounting surface 112 of the herein described insulating support 110. The mounting fixture 120 is configured to retain a sensor 130, e.g., a rigid sensor. As used herein, the term "rigid" refers to any sensor that is not capable of fully conforming to follow the motion of the body part that a sensor such as sensor 130 is intended to measure. In the example shown, the mounting fixture 120 includes a cavity having two diametrically opposed slots 125 adapted to receive corresponding mounting tabs 135 protruding from the outer periphery of the rigid sensor 130. It will be understood that the number of slots and tabs can easily be varied as can the position of the various mounting elements of the sensor and the mounting fixture. Although slots and tabs are shown herein, it will be readily apparent that other suitable connection techniques can be utilized between the rigid sensor 130 and mounting fixture 120 for purposes of retention, including but not limited to screw terminals, quarter-turn fasteners, snap-fits, swing latches, twist-and-turn connections, bayonet-type connections, dovetail-twist connections, magnetic couplings, hook-and-loop fasteners, straps, elastic bands, and/or bracelet clips or any other means that provides adequate and stable retention.

Figure 1B:
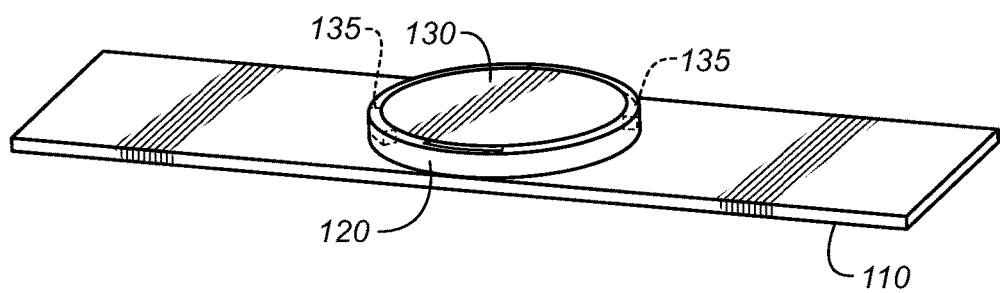
FIG. 1B is a perspective view of the exemplary sensor of FIG. 1A retained by a mounting fixture on the insulating support.

FIG. 1B is a perspective view showing the rigid sensor 130 removably mounted in the cavity of the mounting fixture 120, and disposed such that the rigid sensor 130 is spaced apart from the body 1138 wherein the compliant contact surface 111 is configured for contact with the surface of the body with the rigid sensor 130 being situated on the opposing mounting surface 112. In the herein depicted embodiment, a bayonet type connection is provided in which the mounting tabs of the sensor 130 are initially disposed in the slots 125 and then the rigid sensor 130 is rotated, fixing the tabs within longitudinal portions of the slots disposed beneath the lip of the mounting fixture 120 to retain the sensor 130. The mounting fixture 120 can be a standardized fixture, and various different types of sensors 130 can be designed to mate with the mounting fixture 120 and in which each retained sensor, including the insulating support and mounting fixture can define a sensor carrier 100.

In various embodiments, a physiological monitoring system is defined by the assembled structure shown in FIG. 1B;

that is, the sensor 130 is mounted within the mounting fixture 120 of the insulating support 110. The insulating support 110 is adapted to retain the sensor carrier 100 in position with respect to a respective part of a body 1138, FIG. 11.

Figure 2:
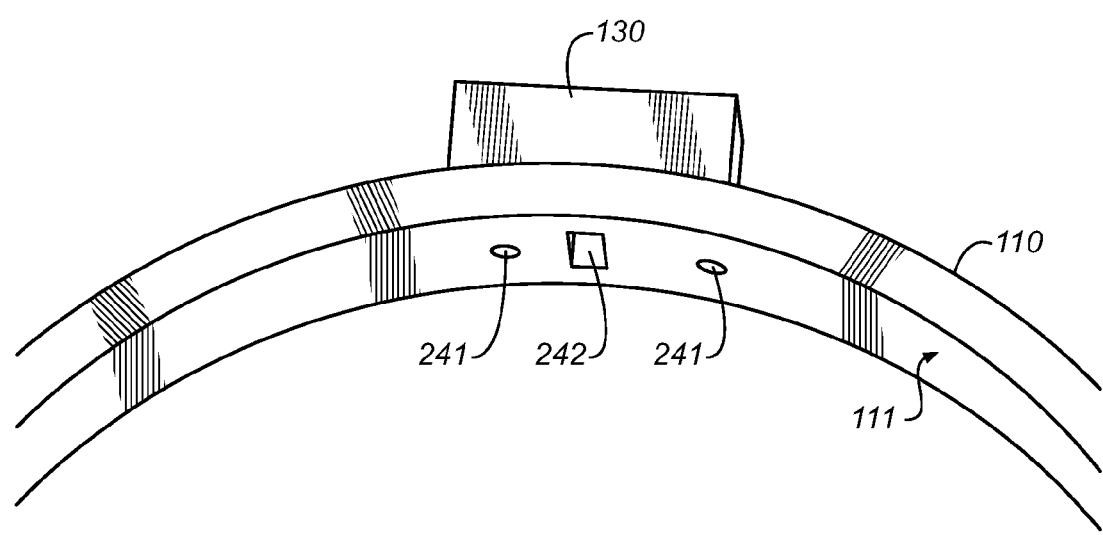
FIG. 2 is a perspective view of an exemplary sensor mounted to an exemplary insulating support.

Referring to FIG. 2, at least one conductive element 241 is arranged at least partly on or over the skin-facing (body) surface 111. As shown, the rigid sensor 130 mounts within the mounting fixture 120 of one of the sensor carriers 100 to determine a physiological property of the body via the at least one corresponding conductive element 241. In this way, the sensor 130 can be used with a variety of sensor carriers, e.g., at different locations on the body. Each sensor carrier 100 can include a circumferential band configured to wrap around a part of the body 1138, e.g., as discussed below with reference to FIGS. 4 and 9. Each sensor carrier 100 can include or be composed of disposable or non-disposable materials. Each mounting fixture 120 can include a quick-disconnect receptacle and the mounting connector include a mating quick-disconnect plug to permit releasable attachment between the sensor and the insulating support 110. For example, in FIG. 1A, the mounting connector may have at least one mating tab (e.g., a living hinge) that can mate with a corresponding tab(s) or recess in the body of the rigid sensor 130, and vice versa, for a secure connection.

Specifically, an active device in the sensor 130 is coupled to the at least one conductive element 241, 242, as discussed below with reference to FIG. 6. Each of the conductive elements 241, 242 conducts energy of a type appropriate to the property to be sensed. In this specific example, the conductive elements 241 are electrical conductors and the conductive element 242 is an optical conductor, e.g., a window or light pipe. The sensor 130 can measure electrical properties of the body 1138 via the electrically-conductive elements 241, e.g., to measure skin resistance. The sensor 130 can also transmit and receive light via the optically-conductive element 242, e.g., to measure blood oxygen content in a reflective configuration (see, e.g., FIG. 6). Optically-conductive elements can include optically transparent or transmitting materials such as glass, optical plastics, or flexible, conformable liquid injection-molded (LIM) silicone. Thermally-conductive elements can include heat pipes, lengths of metal, or patterns of thermally conductive plastic. Electrically-conductive elements can include electrically-conductive materials such as copper or carbon, or electrically-conductive plastics.

As discussed previously, the contact surface 111 and the conductive elements 241, 242 contact the body 1138, but the sensor 130 advantageously does not. Accordingly, to remove oil or sweat fouling, the sensor 130 can easily be detached from the insulating support 110 and the insulating support 110 can be washed. The sensor 130 can then be reattached to the insulating support 110. In this way, cleaning can be performed without negative effects on the sensor 130. Accuracy of measurements can thus be maintained over time. Moreover, the support 110 can be disposable. For example, the support 110 can be discarded following use and the sensor 130 can be attached to a new, clean support 110. This interchangeability permits the use of relatively expensive sensors 130 with relatively inexpensive insulating supports 110.

In several herein described examples, the conductive elements 241 are electrically conductive and the support 110 is electrically insulating. The sensor 130 includes electrical contact interfaces coupled to the respective conductive elements 241 when the sensor 130 is mounted in the mounting fixture 120, FIG. 1B. For example, each of the conductive elements 241 can include a plurality of electrically-conductive fibers configured so that the support 110 is substantially watertight and is electrically conductive along the fibers. Anisotropic conductors, such as those used to connect displays and circuit boards in watches and other portable devices, can be used.

The optically-conductive element 242 can be, e.g., a flexible optical member or extension acting as an optical light pipe. The provision of this element therefore permits flexible, close contact to the skin while housing the more expensive and complex optical emitters and receivers away from the skin inside the sensor 130. The optical members (e.g., the conductive element 242) can include a flexible, conformable liquid injection molded (LIM) silicone shaped into extensions shaped and configured to provide a desired optical transmission. The refractive index of optical components in the sensor 130 can be matched to the plastic or elastomeric extensions to improve optical efficiency. Other transparent and optical materials can be used. Optical filters can also be incorporated in the sensor 130. In various embodiments, the sensor 130 or the band (support 110), e.g., the conductive element 242, includes an optical filter (not shown) disposed between the conductive element 242 and an electro-optical interface of the sensor 130 (discussed below with reference to FIG. 4). This inclusion can permit compensating for variations in measured data corresponding to, e.g., skin color, hair color, or levels of sweat. For example, the filters can be customized to the user for skin tone or for detection at various times of the year (e.g., a suntanned skin tone during summer months). The optical filters can also be customized to the particular body position for the support 110. For example, the arm or wrist area may have a higher concentration of hair than the area comprising the head or chest. To improve sensor accuracy, filters in these sensors 130 could compensate for this higher hair concentration, along with the fineness and color of the hair.

Figure 3A:
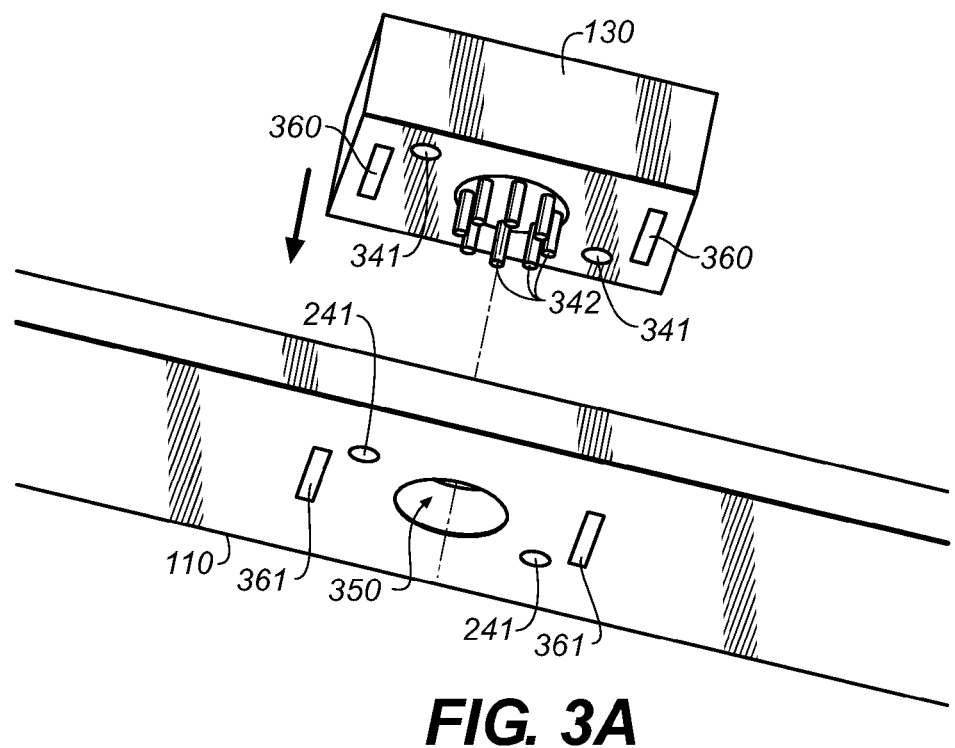
Figure 3B:
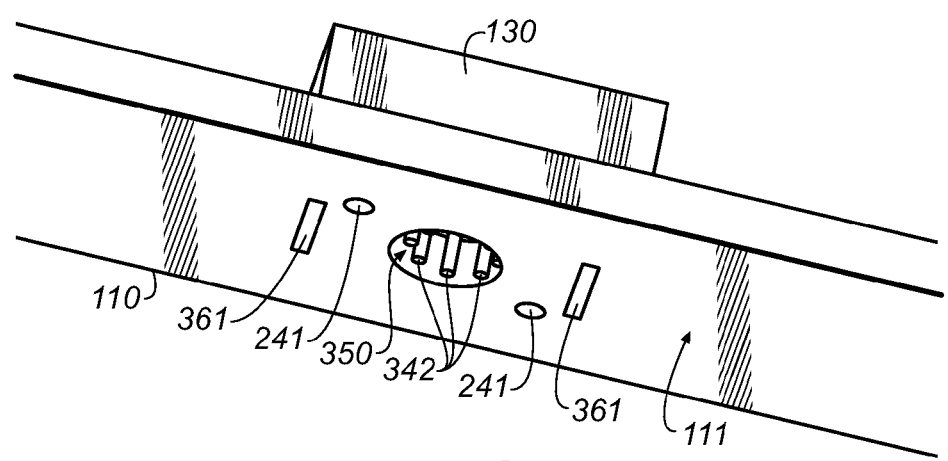

FIGS. 3A and 3B are perspectives of another exemplary rigid sensor 130 and an exemplary insulating support 110, showing the sensor in an unassembled and a mounted configuration, respectively. For purposes of this embodiment and clarity as to the salient features, similar parts are herein used with the same reference numerals According to this embodiment, the sensor 130 includes two interfaces 341 on a lower or bottom surface that are coupled to the conductive elements 241 of the insulating support 110 when the sensor 130 is mounted thereto. The sensor 130 can be configured to determine the physiological property of the body 1138 by providing an excitation to the body 1138 via a first selected one of the conductive elements 241 and receiving a response of the body 1138 to the provided excitation via a second selected one of the conductive elements 241. Any number ≥2 of conductive elements can be used. In this example, the conductive elements 241 extend radially through the thickness of the support 110, which according to this specific embodiment is entirely compliant. In general, at least one of the conductive elements 241 can extend at least in part radially through the compliant support 110.

In this example and for purposes of retaining the sensor 130 to the insulating support and more particularly the mounting surface thereof, the sensor 130 includes a pair of magnets 360 in spaced configuration along the bottom surface thereof that are configured to attract corresponding magnets 361 disposed in the insulating support 110. The magnets 360, 361 can be arranged so that the magnets 360 will repel the magnets 361 if the sensor 130 is rotated 180°. This advantageously provides keying of the mounting of the sensor 130. The magnets 361 and the conductive elements 241 can be co-molded with a compliant, insulating material to form the support 110.

Several conductive elements 342 are shown permanently mounted to the sensor 130. The support 110 includes a through hole or aperture 350 through which the conductive elements 342 can extend when the sensor 130 is mounted to the support 110 in order to determine the physiological property of the body. The conductive elements 342 can be compliant or elastomeric, e.g., silicone light pipes, to provide improved patient comfort. In one example, the sensor 130 can measure the resistance between the conductive elements 241 to determine whether the sensor is attached to a support 110 in contact with a body 1138, FIG. 11. If so, the sensor 130 can measure optical or other properties of the body, e.g., reflectance, using the conductive elements 342.

Referring to FIG. 3B and as attached, the distal ends of the conductive elements 342 protrude to or beyond the contact surface 111 of the insulating support 110. In this way, the conductive elements 342 are arranged at least partly on or over the contact surface 111, even though they are not directly mechanically connected to the contact surface 111 of the herein described support 110.

Figure 4:
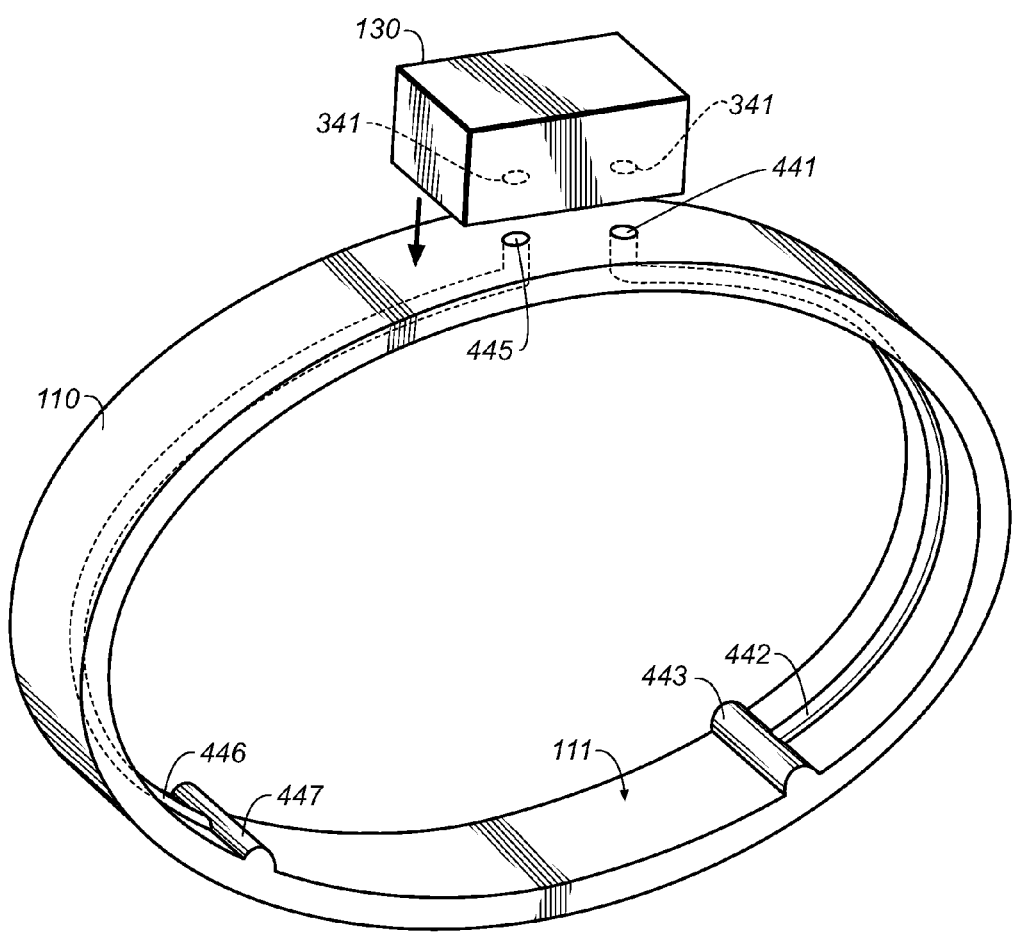
FIG. 4 is a perspective view of an exemplary sensor and insulating support having extended conductive elements.

FIG. 4 is a perspective of another exemplary sensor and an exemplary insulating support having extended conductive elements. As in the preceding, similar parts are herein labeled with the same reference numerals. According to this example, the insulating support 110 is defined by a circumferential band (shown) configured to be wrapped about a portion of the body of a subject (not shown in this view), and in which the contact surface 111 of the support 110 is configured to contact the subject's skin. The sensor 130 includes respective interfaces 341 configured to couple to respective conductive elements, including a pair of conductive segments 441, 445 extending radially through the support 110, when the sensor 130 is mounted to the mounting surface of the support 110.

Still referring to FIG. 4, the conductive segment 441 is coupled to a circumferentially extending conductive segment 442 extending along the contact surface 111 and conductive segment 442 is coupled to a conductive segment 443. For purposes of this description, segment 441 forms a proximal (first) end and conductive segment 443 forms a distal (second) end of a conductive element including the coupled segments 441, 442, 443. Similarly, a second conductive element includes a proximal conductive segment 445, a circumferential conductive segment 446 extending along the contact surface 111, and a distal conductive segment 447. It will be readily understood that the number of conductive segments including those leading to the sensor can easily be varied. According to this exemplary embodiment, the distal conductive segments 443 and 447 are spaced from one another wherein the conductive segments 441, 442, 443, 445, 446, 447 themselves can be fabricated, e.g., by insert molding or bi-component molding. Alternatively, the conductive segments 441, 442, 443, 445, 446, 447 can be affixed to the support 110 via a secondary operation such as welding or fastening with adhesive. Additionally, the conductive segments 442, 446 can be shielded by coating them with a reflective material or by overmolding them with colored elastomer or other suitably opaque or optically-insulating material.

In this example, the conductive elements are light pipes or waveguides conveying light and extending along the contact surface 111. More specifically, light is conveyed by total internal reflection between the conductive segments 441 and 443. In this way, the sensor 130, via the interfaces 341, can determine the physiological property of the body at the distal ends of the conductive elements, i.e., at the conductive segments 443, 447. This can be useful, e.g., for a transmission-mode pulse oximeter. The sensor 130 can transmit light via one of the interfaces 341 into the conductive segment 441. Such light will be emitted into the body (not shown in this view) from the conductive segment 443 and substantially not from the location of the sensor 130. Some of the light will pass through the body, be collected by the conductive segment 447, and then travel to the conductive segment 445, into the other of the interfaces 341, and back to the sensor 130. This routing of conductive elements advantageously permits positioning the sensor 130 away from the area to be measured if, e.g., the sensor would obstruct the patient's motion if placed near the area to be measured.

In various examples, the conductive elements (e.g., light pipes) are arranged only over the contact surface 111. In other examples, the insulating support 110 includes a hole 350, FIG. 3B, and the conductive elements extend part or all of the way through the hole 350. In general, one or more of the conductive elements can be optically conductive at a selected wavelength. The sensor 130 can include respective electro-optical interface(s) 342, whether transmitter, receiver, or both, coupled to respective conductive element(s) when the sensor 130 is mounted in the mounting fixture 120, FIG. 1B. Multiple interfaces 341, e.g., one transmitter and one receiver, can be coupled to a single conductive element or segment, e.g., the conductive segment 441.

Figure 5A:
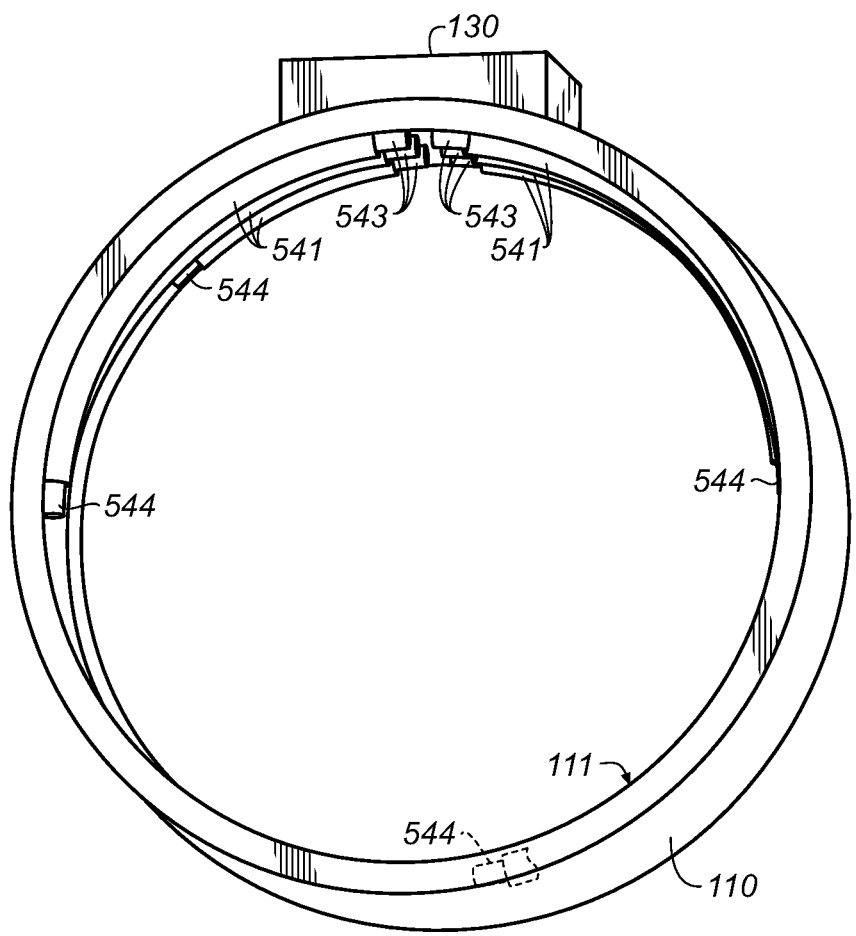
FIGS. 5A and 5B depict elevational and partial perspective views, respectively, of an exemplary sensor and insulating support having extended conductive elements.
Figure 5B:
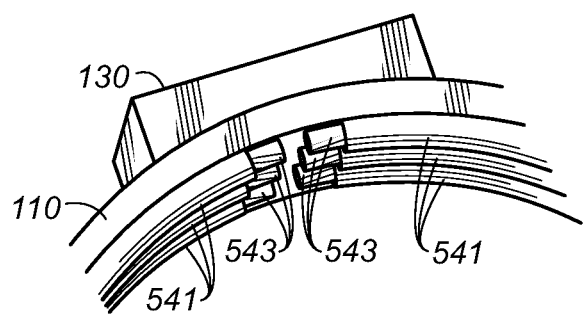

Referring to FIGS. 5A and 5B, another exemplary sensor and insulating support arrangement are herein described. The exemplary insulating support 110 according to this embodiment includes a plurality of extended conductive elements 541 that are disposed in a substantially parallel and generally circumferential manner about the insulating support 110, which is also a circumferential member. Each of the conductive elements 541 (in this example, optical fibers or other light pipes having a core surrounded by cladding, e.g., elastomeric overmolding), has a proximal end 543 coupled to a mounted rigid sensor 130. The conductive elements 541 extend circumferentially along the contact surface 111 and terminate at distal ends 544, each having varying lengths and defining different measuring positions. As such, the distal ends 544 are spaced apart from each other.

FIG. 5B shows an enhanced view of the area around the sensor 130. The cladding of each optical fiber has been cut back at least in part to expose the fiber core at the proximal ends 543. This cut back permits the sensor 130 to optically couple to each of the parallel conductive elements 541. The sensor 130 can activate or select various combinations of the conductive elements 541 to take measurements of various areas of the body (not shown) In the example shown in FIG. 5A, the distal ends 544 are located approximately at 90°, 170°, 270°, and 315° clockwise from the sensor 130. More specifically, the sensor 130 can activate or select the light pipes having the distal ends 544 at approximately 90° and approximately 270° to measure directly through a part of the body 1138. The sensor 130 can alternatively activate or select the light pipes having the distal ends 544 at approximately 270° and approximately 315° to take a reflective blood oxygen measurement of an artery close to the skin of the body, e.g., a finger placed through the ring-shaped support 110. In this example, the conductive elements 541 are arranged in planes normal to the axis of the body portion (e.g., wrist, finger) extending through the ring-shaped support 110. Each plane includes one conductive element 541 selectively coupleable to a light emitter in the sensor 130 and one conductive element 541 selectively coupleable to a photoreceiver in the sensor 130. Other suitable arrangements can easily be contemplated.

The sensor 130 can select the conductive elements 541 in various ways. In an example, the sensor 130 includes a respective light emitter (e.g., an LED) coupled to each of the conductive elements 541 through which light can be selectively transmitted. The sensor 130 electronically directs current through a desired one of the light emitters. The sensor 130 also includes a respective photodiode coupled to each of the conductive elements 541 through which light can be selective received. The sensor 130 can include a multiplexer or other structure to receive data only from selected photodiode(s). In another example, the sensor 130 can include one or more optical switches (e.g., electronically-controllable shutters) to selectively direct light between an LED or photodiode and one or more of the conductive elements 541. Any number of light emitters or photodiodes can be used with any number of conductive elements 541, and one or more than one of the conductive elements 541 can be coupled to selected LED(s) or photodiode(s) at a given time. It should be understood that though this exemplary embodiment relates to optical light transmission, the concepts can equally apply to other energy forms, e.g., voltage sources and detectors, and relays or transistors to direct current through various electrically-conductive elements.

Figure 6:
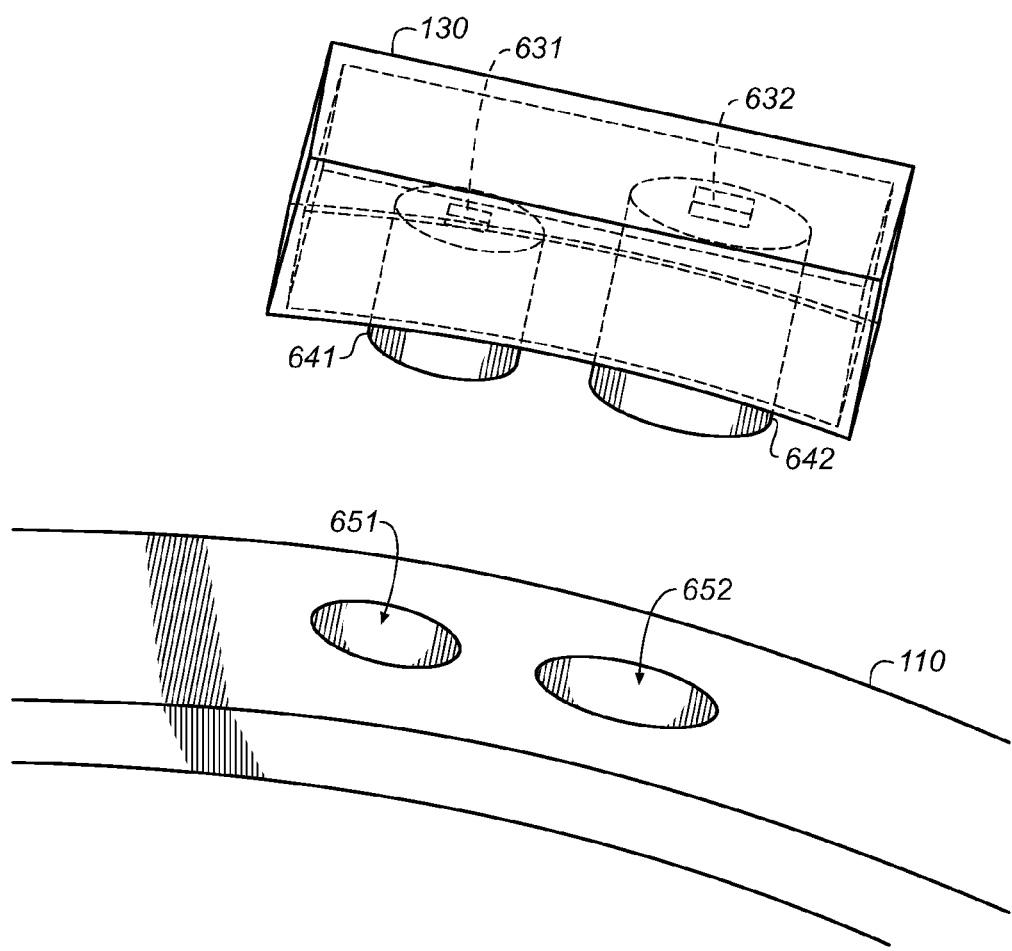
FIG. 6 is a perspective view of another exemplary sensor and insulating support.

FIG. 6 is a perspective view of yet another exemplary sensor 130 and an exemplary insulating support 110. For purposes of this embodiment, the insulating support 110 has two holes 651, 652 extending through the thickness of the insulating support 110. The corresponding sensor 130 includes two active devices 631, 632, engaged with conductive elements 641 and 642 extending through a bottom or engagement surface of the sensor 130. The active devices 631, 632 include components that provide energy or perform measurements via the conductive elements 641, 642. Exemplary components can include LED, photodiodes, voltage sources, pressure sensors, ammeters, galvanometers, or electronic temperature sensors. Throughout this disclosure, including above, references to coupling the sensor 130 to a conductive element signify that an active device in the sensor 130 is coupled to that conductive element. Though this embodiment specifically includes two active devices and two holes, it will be understood that the number can be suitably varied.

In this specific example, the rigid sensor 130 is a reflection-mode pulse oximeter, the active device 631 is an LED, and the active device 632 is a photodiode. The sensor 130 also includes optically-conductive elements 641, 642 coupled to the respective active devices 631, 632 and configured to fit through the respective holes 651, 652 when the sensor 130 is coupled to the support 110. The conductive elements 641, 642, and likewise the active devices 631, 632, can be optically isolated from each other within the sensor 130 by an inner shield, e.g., a metallic foil or another highly reflective material (not shown). Examples of this shielding are discussed below in greater detail with reference to FIG. 7B.

Figure 7A:
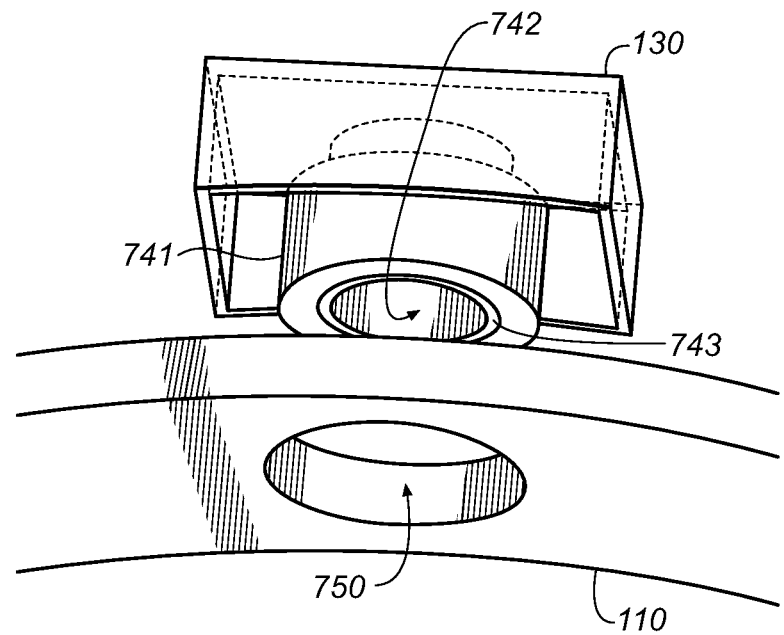
FIGS. 7A and 7B are perspective views of yet another exemplary sensor and insulating support.
Figure 7B:
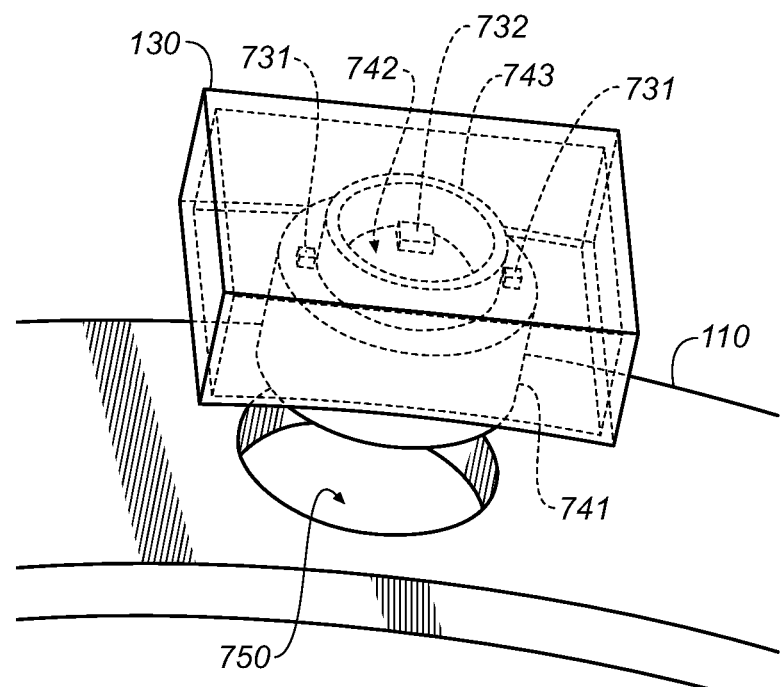

FIGS. 7A and 7B are top and bottom perspective views of another exemplary sensor 130 and insulating support 110. Referring to FIG. 7A, insulating support 110 is defined with a through hole 750 extending between the skin contacting surface and the mounting surface. The rigid sensor 130 is sized to at least partially fit within the hole 750 and includes three concentric conductive elements; namely, a pair of optically-conductive elements 741 and 742, and an electrically-conductive element 743. Referring to FIG. 7B, the optically conductive element 741 is coupled to two active devices 731, e.g., LEDs in the sensor, shown in phantom. The remaining optically conductive element 742 is coupled to another active device 732, e.g., a photodiode, and can include spherical optics or other focusing elements. The electrically conductive element 743 is also coupled to an active device (not shown), e.g., a voltage source.

The electrically-conductive element 743 can be, e.g., a metal foil, or a backer such as a plastic sheet coated with a reflective or mirrored material on at least one side, or incorporating such a material in a matrix. The plastic sheet can also be coated with or incorporate into a matrix, an electrically-conductive material. In various aspects, the electrically-conductive element 743 is also thermally conductive (e.g., copper) so that the conductive element 743 can be used for both temperature and current sensing. The conductive element 743 can be divided into a plurality of electrodes separated by electrically-insulating, reflective spacers (not shown).

In another aspect, a composite material is used for either of the conductive elements 741, 742. The composite material can include optically and electrically-conductive materials, together or in zones. A composite material can be hybrid-molded or machined. An encapsulated emulsion that is both optically and electrically conductive can also be used.

In various aspects, the electrically-conductive element 743 serves as a light pipe. This concentrates the contact with the body in a small area. Additional conductor/light-pipe dual-purpose structures can also be used.

In functional use using photo plasmography with LEDs and photodiodes, the optical barrier/shield can also function as an electrode. This additional functionality is in contrast to many prior schemes, which require separate shielding and electrically-conductive members. In this and other examples, the conductive elements that isolate the active units from the skin are in the replaceable module of the sensor 130 rather than in the support 110, although these components can also be located in the support 110.

Figure 8:
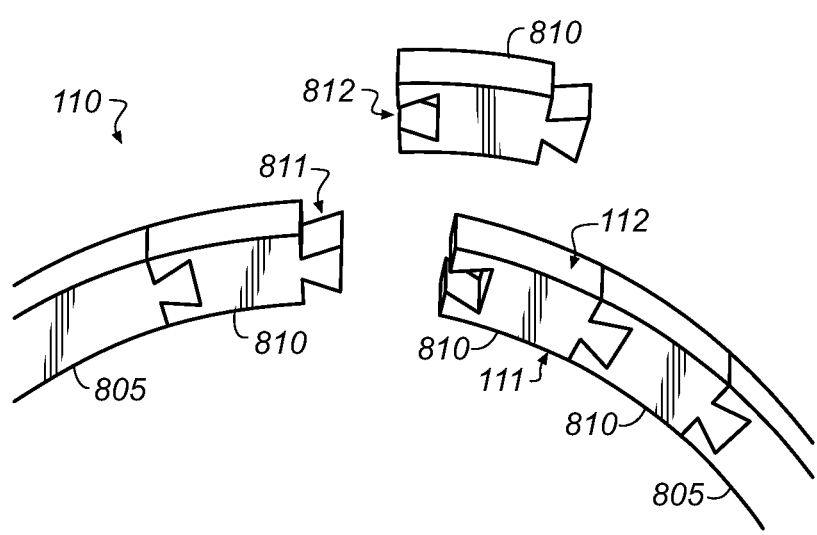
FIGS. 8 and 9 are perspective views of insulating supports having interlocking modules according to various embodiments.

FIG. 8 presents a partial perspective of yet another exemplary insulating support 110. According to this version and rather than having a support constructed as a single homogeneous member, a plurality of substantially-insulating and interlocking modules 805, 810 can be provided. In the example shown, the insulating support 110 includes four modules 810 and two sizing modules 805. Each of the modules 805, 810 occupies a respective circumferential portion of the compliant contact surface 111 and of the mounting surface 112. The sizing modules 805 in this example have such portions consisting of insulating material, but they can include some conductive material over the contact surface 111 in various embodiments.

Male mating connectors 811 provided at one end of the module 810 and having outwardly tapering ends are configured to interlock with corresponding female mating connectors 812 at one end of the module 810 to interlock a pair of adjacent modules 805, 810. In general, each of the modules 805, 810 can include a first mounting end and a second, mating mounting end of the module 805, 810 opposite the first end. The first mounting end of each of the modules 805, 810 is releasably connected to the second mounting end of an adjacent module 805, 810. The modules 805, 810 can be interlocked to form any form of circumferential body worn member such as but not limited to a wristband or headband.

Figure 9:
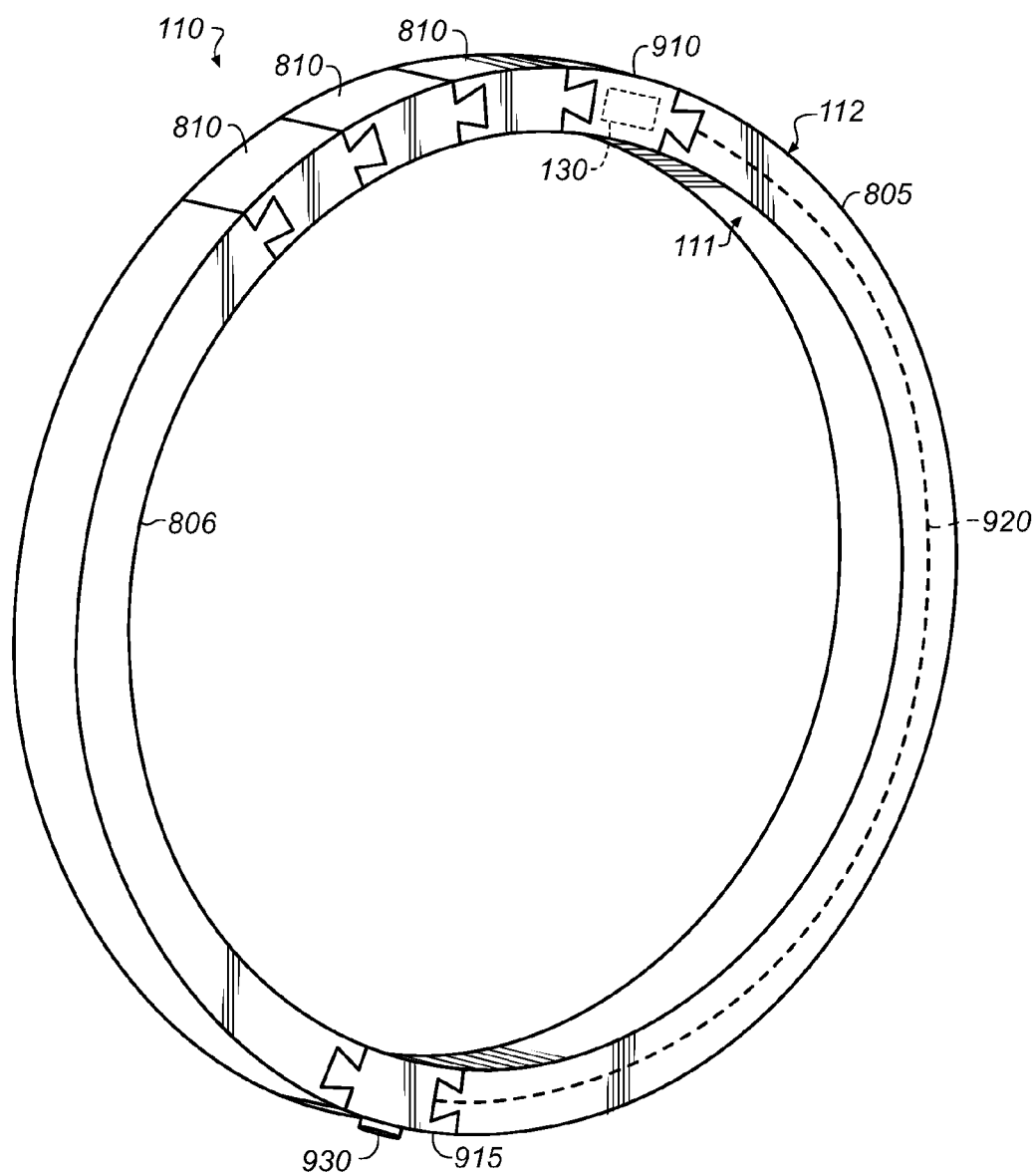

FIG. 9 depicts a perspective view of an insulating support 110 having a plurality of interlocking modules 805, 806, 810, 910, 915. In this example, a rigid sensor 130 (shown in phantom) is disposed within the module 910 and is spaced apart from the contact surface 111 thereof. The module 915 has a mounting fixture 120, FIG. 1A, and is retaining a second rigid sensor 930. The sensor 930 is configured to cooperate with the sensor 130 to determine the physiological property of the body via the at least one conductive element (e.g., the conductive element 743, FIG. 7A). For example, the sensors 130 and 930 can include respective electrodes to measure an ECG voltage.

In an example, the physiological property is a blood oxygen content. According to this embodiment, the sensor 130 includes one of a light emitter or a photodetector, and the sensor 930 includes the other. The modules 910, 915 are arranged so that at least some light emitted by the light emitter passes through a part of the body and reaches the photodetector. In this example, the modules 805, 806, 810, 910, 915 are arranged to form a circumferential band and module 915 is diametrically disposed on the opposite side of the band (support 110) from the module 910. In another example, one of the modules 810 can include an active device, and the measurement can be taken using the modules 910, 810.

In another example, sensor 930 is configured to determine a second physiological property of the body different from the physiological property. For example, sensor 130 can be a skin-conductivity sensor having two electrically-conductive elements 241, FIG. 2, and sensor 930 can be an integrated oximeter such as those shown in FIGS. 6-7B. Any number of sensors can be used in any number of modules, and any combination of sensors can be configured for cooperative measurement of a physiological property or independent measurement. In an example, one of the modules 810, 910, 915 can include an accelerometer (not shown) for measuring the motion of the body.

In various embodiments, a channel 920 (shown in phantom) includes one or more conductors, e.g., wires or optical fibers that are configured to convey signals between the diametrically opposed modules 910, 915. For example, photodiode data from the sensor 930 can be conveyed via channel 920 to the sensor 130 in the module 910 for processing. The channel 920 can be disposed lengthwise in or over the module 805. The modules 805 and 806 can be sizing modules, such as those previously discussed.

Figure 10:
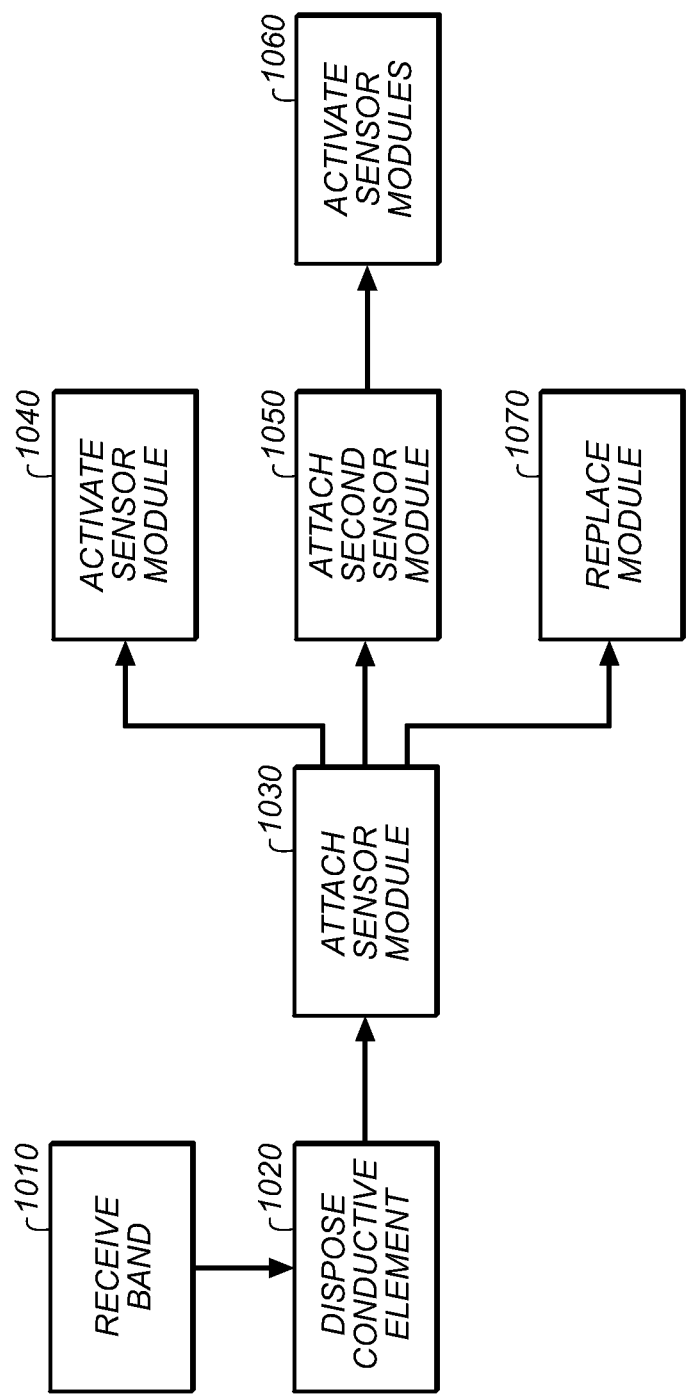
FIG. 10 is a flowchart illustrating exemplary methods for enabling a physiological parameter to be measured or monitored without direct contact between an active device and a body.

FIG. 10 is a flowchart illustrating exemplary methods for enabling a physiological parameter to be measured or monitored without direct contact between an active device (e.g., a pulse monitor) and a body. For purposes of an exemplary embodiment, processing begins with step 1010. For clarity of explanation, reference is herein made to various components shown in FIGS. 1-9 and 11 that can carry out or participate in the steps of the exemplary method. It should be noted, however, that other components can be used; that is, the exemplary method is not limited to being carried out by the identified components.

In step 1010, a substantially-insulating and compliant circumferential band having a skin-contacting inner surface (or skin-facing surface, or contact surface) and an exterior surface (or mounting surface) is received.

In step 1020, at least one conductive element 241 is disposed within the circumferential band. The at least one conductive element 241 is at least partly arranged on or over the inner surface of the band, e.g., the contact surface 111, FIG. 1A of the insulating support 110, FIG. 1A. As discussed above, the conductive element(s) 241 can be offset or recessed, or can extend only along the contact surface 111.

In step 1030, a sensor 130 retaining the active device is attached to the exterior surface of the band, e.g., the mounting surface 112, FIG. 1A. As a result, the sensor 130 is coupled to the at least one conductive element 241. Step 1030 can be followed by any of steps 1040, 1050, or 1070.

In step 1040, the sensor 130 is activated to provide a signal to the body and receive a response of the body to the provided signal.

Step 1050 is useful, e.g., in aspects using a plurality of conductive elements 241. In step 1050, a second sensor 930 retaining a second active device is attached to the exterior surface of the band. As a result, the second sensor 130 is coupled to one of the plurality of conductive elements 241. Step 1050 can be followed by step 1060.

In step 1060, the sensor 130 is activated to provide a signal to the body and the second sensor 130 is activated to receive a response of the body to the provided signal. In this way, the two sensors 130 cooperate to measure the physiological property.

In step 1070, the sensor 130 is detached from the mounting surface of the band. A second, different sensor 130 is then attached in place of the detached sensor 130. This interchangeability permits measuring different physiological parameters using a single band. Referring back to FIG. 9, a user can select sizing modules 805, 806 of appropriate lengths to fit the support 110 comfortably to a part of the body 1138 that is to be measured. Different types of measurements can then advantageously be taken without requiring the user to reconfigure or re-size the support 110.

Figure 11:
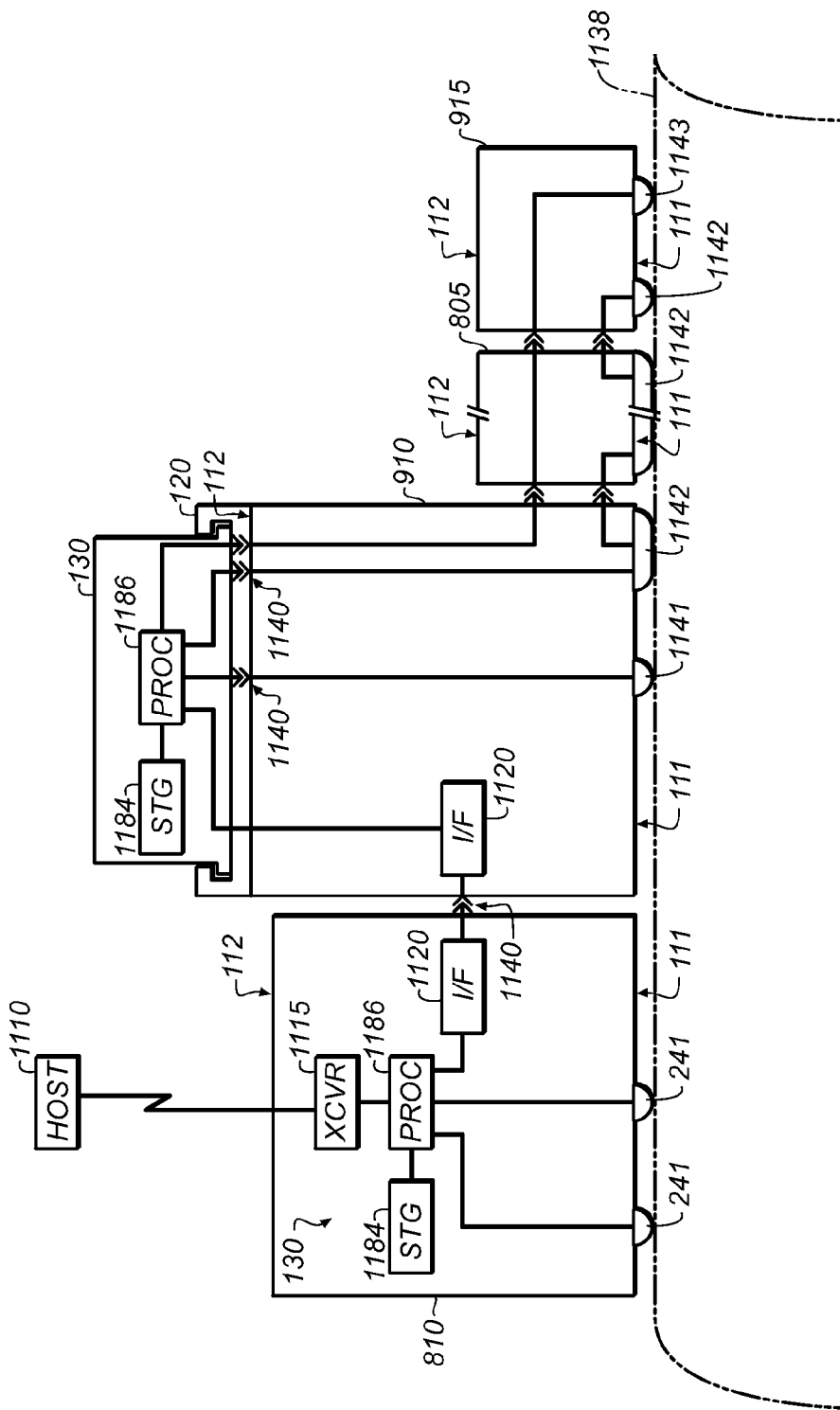
FIG. 11 is a block diagram of an exemplary system for measuring a physiological property of the body of a user or patient.

FIG. 11 is a block diagram of an exemplary system for measuring a physiological property of the body 1138 of a user. A skin surface of the body 1138 is shown schematically. This block diagram is represented as a schematic side view of an insulating support 110, FIG. 9, including a plurality of interconnected modules 810, 910, 805, 915. The module 805 is a sizing module. The modules 810, 910, 905, 915 are interlocked as shown in FIG. 9; the interlocks are omitted from this figure for purposes of clarity.

In this example, the module 810 includes the sensor 130 spaced apart from the contact surface 111. The sensor 130 includes a transceiver 1115 configured to communicate determined physiological data to a host processor 1110. The communication can be, e.g., wired or wireless. The host processor 1110 can be, e.g., a personal computer, smartphone, tablet computer, or belt-mounted data-collection device. The sensor 130 also includes a processor 1186 and a storage device 1184, discussed below. In various aspects, sensors can be integrated into interlocking modules or mounted external to those modules.

The modules 810, 910 include respective interfaces 1120 coupled to a conductor between the modules 810, 910. The interfaces 1120 are connected to respective processors 1186 in the modules 810, 910 so that the modules 810, 910 include respective conductors configured to convey signals between each other. A connector 1140, represented graphically as a double arrowhead, couples the respective conductors of the modules 810, 910, e.g., when the modules 810, 910 are mechanically interlocked. The connector 1140 can include pads, bumps, pogo pins, spring contacts, or other electrical connectors. The connector 1140 can transfer data unidirectionally or bidirectionally.

In this example, the module 910 includes a mounting fixture 120. The corresponding sensor 130, with its processor 1186 and storage device 1184, is mounted in the mounting fixture 120 and is coupled via connectors 1140 to, e.g., conductive elements 1141, 1142, 1143. The interface 1120 of the module 910 can be disposed in or on the module 910 or the coupled sensor 130.

The conductive element 1141 is arranged over the contact surface 111 only of the module 910. However, the conductive element 1142 includes one or more conductive segments, as shown, arranged in or over respective modules 910, 805, 915 and coupled between interlocked modules via connectors 1140 (double arrowheads; for clarity, not labeled). In another example, the processor 1186 associated with the module 910 is connected via connectors 1140 through module 805 to the conductive element 1143 in the module 915. The module 805 passes this connection through the module 805 but does not expose the connection to the body 1138. This is an example of the channel 920, FIG. 9.

The processor 1186 includes one or more data processor(s) that implement processes of various embodiments described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise. The phrase "communicatively connected" includes any type of connection, wired or wireless, between devices, data processors, or programs in which data can be communicated. Subsystems such as the storage device 1184 and the user interface are shown separately from the processor 1186 but can be stored completely or partially within the processor 1186.

The storage device 1184 includes or is communicatively connected with one or more tangible non-transitory computer-readable storage medium(s) configured to store information, including the information needed to execute processes according to various embodiments. The term "device" does not imply that storage device 1184 include only one piece of hardware that stores data. A "tangible non-transitory computer-readable storage medium" as used herein refers to any non-transitory device or article of manufacture that participates in storing instructions which may be provided to the processor 1186 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM).

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct the processor 1186 to perform a particular series of operational steps when loaded, thereby implementing functions or acts specified herein such as measuring physiological properties or characteristics of the body 1138.

In an example, the storage device 1184 includes a random-access memory (RAM) and a disk or other tangible computer-readable storage device such as a hard drive or a solid-state flash drive. Computer program instructions are read into the RAM from the storage device, or a wireless, wired, optical fiber, or other communications port. The processor 1186 then executes one or more sequences of the computer program instructions loaded into the RAM, as a result performing process steps and other processing described herein. In this way, the processor 1186 carries out a computer implemented process that provides technical effects described herein, e.g., determining physiological characteristics of a patient's body 1138. For example, blocks of the flowchart illustrations or block diagrams herein, and combinations of those, can be implemented by computer program instructions. The RAM can also store data used by running programs.

Program code to carry out methods described herein can execute entirely on a single processor 1186 or on multiple communicatively-connected processors 1186. For example, code can execute wholly or partly on a user's computer and wholly or partly on a remote computer, e.g., a server. The remote computer can be connected to the user's computer through a network. The user's computer or the remote computer can be non-portable computers, such as conventional desktop personal computers (PCs), or can be portable computers such as tablets, cellular telephones, smartphones, or laptops.

The sensor 130 or the host processor 1110 can include a user interface (not shown). The user interface can include a display device, a touchscreen, a processor-accessible memory, or any device or combination of devices to which data is output by or input to the processor 1186. For example, the user interface can include one or more touchscreen(s), speaker(s), buzzer(s), vibrator(s), button(s), switch(es), jack(s), plug(s), or network connection(s).

In various embodiments, the processor 1186 or the host processor 1110 is communicatively connected to a network, e.g., via a communications interface or transceiver (not shown). The processor 1186 can send messages and receive data, including program code, to and from the network. For example, requested code for an application program (e.g., a JAVA applet) can be stored on a tangible non-volatile computer-readable storage medium connected to the network. A network server (not shown) can retrieve the code from the medium and transmit it via the network to the processor 1186. The received code can be executed by the processor 1186 or the host processor 1110 as it is received, or stored in the storage device 1184 for later execution.

Various aspects include a system having multiple sensors 130 and one washable, reusable band (e.g., the support 110). This permits taking different types of measurements without having to resize the band.

In various aspects, a biomedical measuring device includes a circumferential band that is configured to be wrapped about a portion of a subject's body, the band including an inner body (skin-contacting or -facing) surface and an opposed outer surface, the band being substantially insulating; at least one conductive element extending radially through the circumferential band; and a sensor attached to the circumferential band and coupled to the at least one conductive element. The band can include a compliant (e.g., elastic) material around the circumference of the band. The sensor can be releasably attached to the exterior surface of the band.

Each of the sensor and the band can include corresponding attachment features. The attachment feature of the sensor being can be, e.g., a magnet, a dove-tail connector, a bayonet connector, a threaded connector, an adhesive, a hook portion of a hook-and-loop fastener, or a loop portion of a hook-and-loop fastener.

The sensor can be disposed within the band and spaced apart from the inner contact surface 111. This is as described above with reference to the module 810, FIG. 11. The band can comprise a plurality of interlocking sections (FIG. 9), one of the interlocking sections including the sensor and the at least one conductive element. The conductive element can include at least one optical element. The at least one optical element can include a light pipe formed within the band. The at least one optical element can include two light pipes formed within the band, each having a respective proximal end coupled to the sensor, the distal ends of the light pipes being spaced apart from each other. The sensor can include a physiological parameter sensor configured to sense a physiological parameter, e.g., surface body temperature, core body temperature, heart rate, blood oxygen content, blood pressure, respiration rate, or electrocardiogram signals. The conductive element can include an electrically conductive element and the circumferential band can be substantially electrically insulating. The circumferential band can be configured to be worn about at least one of a finger, wrist, arm, leg, head, or torso of the patient.

According to various embodiments, a biomedical device (e.g., for home therapy; over the counter or doctor-prescribed) can include a compliant, substantially insulating support having a contact surface (contact surface 111) and an opposed mounting surface 112. A conductive element 241 can extend through the compliant support from the contact surface to the mounting surface. A mounting fixture can be disposed over the mounting surface and configured to retain a rigid sensor 130 in position to communicate with the conductive element. The rigid sensor retained in the mounting fixture can be included in the biomedical device, so that the rigid sensor determines physiological properties via the conductive element. The sensor can participate with other sensors in taking the measurement; this is included in "determining" herein. For example, the sensor can include the LED but not the photodiode of a pulse oximeter, and the photodiode can be included in a different sensor (e.g., FIG. 9).

The device can include a second conductive element 241 extending through the compliant support 110 from the contact surface to the mounting surface so that the rigid sensor determines physiological properties via the conductive element and the second conductive element. This useful, e.g., for two-electrode voltage measurements.

Integrated sensors 130 according to various aspects can include multiple pickups and corresponding conductive regions. This permits reading, e.g., temperature and optical properties with one sensor. The sensor position can be fixed on the band or other support 110. The measurements do not have to be under the sensor, e.g., as discussed above with reference to FIG. 4; this permits accurate measurements to be taken with small sensors.

PARTS LIST FOR FIGS. 1-11

110 support
111 contact surface
112 mounting surface
120 mounting fixture
125 slot
130 sensor
135 tab
140 connector
241, 242 conductive elements
341 interface
342 conductive element
350 hole
360, 361 magnets
441, 442, 443, 445, 446, 447 conductive segments
541 conductive element
543 proximal end
544 distal end
631, 632 active devices
641, 642 conductive elements
651, 652 holes
731, 732 active devices
741, 742, 743 conductive elements
750 hole
805, 806 sizing modules
810 module
811, 812 connectors
905, 910, 915 modules
920 channel
930 sensor
1010, 1020, 1030, 1040, 1050 steps
1060, 1070 steps
1110 host processor
1115 transceiver
1120 interface
1138 body
1184 storage device
1140 connector
1141, 1142, 1143 conductive elements
1184 storage device
1186 processor While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Separate references to "an embodiment" (or "aspect" or "example") or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. To the extent there are variations of the invention that are within the spirit of the disclosure or are equivalent to the inventions found in the claims, it is the intent that this patent will cover those variations as well.

What is claimed is:

1. A method for enabling a physiological parameter to be measured or monitored without direct contact between an active device and a body, the method comprising:

receiving a substantially-insulating circumferential band having a skin-contacting inner surface and an exterior surface;

disposing at least one conductive element within the circumferential band, the at least one conductive element at least partly arranged on or over the inner surface of the band; and attaching a sensor retaining the active device to the exterior surface of the band so that the active device is coupled to the at least one conductive element, wherein the at least one conductive element comprises a distal conductive segment positioned on the skin-contacting inner surface and circumferentially away from the sensor such that a signal provided by the sensor can be emitted to the body from the distal conductive segment and substantially not from the location of the sensor.

2. The method according to claim 1, further including activating the sensor to provide a signal to the body and receive a response of the body to the provided signal.

3. The method according to claim 1, wherein the at least one conductive element includes a plurality of conductive elements, the method further including attaching a second sensor retaining a second active device to the exterior surface of the band, so that the second sensor is coupled to one of the plurality of conductive elements.

4. The method according to claim 3, further including activating the sensor to provide a signal to the body and activating the second sensor to receive a response of the body to the provided signal.

5. The method according to claim 1, further including detaching the sensor from the exterior surface of the band and attaching a second, different sensor in place of the detached sensor.

* * * * *